United States Patent
Chotani et al.

(10) Patent No.: US 12,338,478 B2
(45) Date of Patent: Jun. 24, 2025

(54) METHOD FOR INCREASING BACKSET RECYCLE IN DRY GRIND ALCOHOL PRODUCTION

(71) Applicant: DANISCO US INC, Palo Alto, CA (US)

(72) Inventors: Gopal K. Chotani, Cupertino, CA (US); Jaclyn Diana Demartini, Palo Alto, CA (US); Jacob Andrew Latone, San Jose, CA (US); Vivek Sharma, Palo Alto, CA (US); Jayarama K. Shetty, Palo Alto, CA (US)

(73) Assignee: DANISCO US INC., Palo Alto, CA (US)

( * ) Notice: Subject to any disclaimer, the term of this patent is extended or adjusted under 35 U.S.C. 154(b) by 580 days.

(21) Appl. No.: 17/641,507

(22) PCT Filed: Sep. 9, 2020

(86) PCT No.: PCT/US2020/049799
§ 371 (c)(1),
(2) Date: Mar. 9, 2022

(87) PCT Pub. No.: WO2021/050451
PCT Pub. Date: Mar. 18, 2021

(65) Prior Publication Data
US 2022/0333141 A1 Oct. 20, 2022

Related U.S. Application Data

(60) Provisional application No. 62/900,325, filed on Sep. 13, 2019.

(51) Int. Cl.
C12P 7/14 (2006.01)
C12P 19/14 (2006.01)

(52) U.S. Cl.
CPC ............ *C12P 7/14* (2013.01); *C12P 19/14* (2013.01); *C12Y 302/01001* (2013.01); *C12Y 302/01003* (2013.01)

(58) Field of Classification Search
None
See application file for complete search history.

(56) References Cited

U.S. PATENT DOCUMENTS

2009/0117632 A1* 5/2009 Steiner ............... C12P 7/14 435/161
2010/0196994 A1 8/2010 Van Leeuwen et al.
2011/0230394 A1 9/2011 Wiatr et al.
2012/0294981 A1 11/2012 Wicking et al.
2015/0305370 A1 10/2015 Bleyer et al.

FOREIGN PATENT DOCUMENTS

WO 2006/004748 A2 1/2006

OTHER PUBLICATIONS

Kumar, D., et al. Biotechnol Biofuels 9, 228 (2016). https://doi.org/10.1186/s13068-016-0648-1) (Year: 2016).*
Krzywonos, Małgorzata et al. "Aerobic Biodegradation of Wheat Stillage (Distillery Wastewater) at an Elevated Temperature—Effect of Solids Separation." Biochemical engineering journal 49.1 (2010). https://doi:10.1016/j.bej.2009.11.003 (Year: 2010).*
Xinchao Yang, et al. Waste Management, vol. 62, 2017, pp. 241-246, https://doi.org/10.1016/j.wasman.2017.01.040.) (Year: 2017).*
Pietrzak, Witold, and Joanna Kawa-Rygielska. "Backset valorization in dry-grind ethanol process by co-culture of edible filamentous fungi and fodder yeast." Journal of Cleaner Production, vol. 220, May 2019, pp. 376-385, https://doi.org/10.1016/j.jclepro.2019.02.136. (Year: 2019).*
De Souza PM, de Oliveira Magalhães P. Application of microbial α-amylase in industry—A review. Braz J Microbiol. Oct. 2010;41(4):850-61. doi: 10.1590/S1517-83822010000400004. Epub Dec. 1, 2010. PMID: 24031565; PMCID: PMC3769773. (Year: 2010).*
Pasteris, Sergio E., and Ana M. Strasser de Saad. "Sugar-glycerol Cofermentations by lactobacillus hilgardii isolated from wine." Journal of Agricultural and Food Chemistry, vol. 57, No. 9, Mar. 26, 2009, pp. 3853-3858 (Year: 2009).*
International Search Report and Written Opinion from PCT Application No. PCT/US2020/049799 dated Dec. 18, 2020, 10 pages.
Kwiatkowski et al., "Modeling the process and costs of fuel ethanol production by the corn dry-grind process", Industrial Crops and Products, vol. 23, Issue 3, May 2006, pp. 288-296.
Pietrzak et al., "Backset valorization in dry-grind ethanol process by co-culture of edible filamentous fungi and fodder yeast", Journal of Cleaner Production, vol. 220, Feb. 14, 2019, pp. 376-385.
Reis et al., "New technologies in value addition to the thin stillage from corn-to-ethanol process", Reviews in Environmental Science and Bio/Technology, 16, 2017, pp. 175-206.
Wang et al., "Reusing a mixture of anaerobic digestion effluent and thin stillage for cassava ethanol production", Journal of Cleaner Production, vol. 75, 2014, pp. 57-63.

* cited by examiner

*Primary Examiner* — M Franco G Salvoza
*Assistant Examiner* — Benjamin Hall Easton

(57) ABSTRACT

The present invention relates to a dry grind ethanol process in which post-distillation backset is subjected to aerobic fermentation to remove components that are inhibitory to an ethanolagen, such as yeast, allowing the utilization of an increased amount of post-distillation backset during the initial preparation of starch-containing substrates for the dry grind ethanol process. Aerobic fermentation of the post-distillation backset allows substantially higher backset recycle, resulting in fresh water savings and increased sustainability.

11 Claims, 7 Drawing Sheets

METHOD FOR INCREASING BACKSET RECYCLE IN DRY GRIND ALCOHOL PRODUCTION

CROSS-REFERENCE TO RELATED APPLICATION

This application is a U.S. national stage application under 35 U.S.C. § 371 of International Application No. PCT/US2020/049799, filed on Sep. 9, 2020, entitled "METHOD FOR INCREASING BACKSET RECYCLE IN DRY GRIND ALCOHOL PRODUCTION," which claims priority to U.S. Provisional Patent Application No. 62/900,325 filed Sep. 13, 2019, the disclosures of which are incorporated by reference herein in their entireties.

TECHNICAL FIELD

The present invention relates to a dry grind ethanol process in which post-distillation backset is subjected to aerobic fermentation to remove components that are inhibitory to an ethanolagen, such as yeast, allowing the utilization of an increased amount of post-distillation backset during the initial preparation of starch-containing substrates for the dry grind ethanol process. Aerobic fermentation of the post-distillation backset allows substantially higher backset recycle, resulting in fresh water savings and increased sustainability

BACKGROUND

Dry grind ethanol production involves several discrete operations, including grinding, cooking, liquefaction, saccharification, fermentation and separation of liquid and solids to produce alcohol and other co-products. Commonly, whole grain, such as corn, is milled to a fine particle size and then mixed with, among other liquid components, various recycled liquids in a series of mix boxes and slurry tanks. The resulting grain slurry is subjected to high temperatures in a jet cooker (or milder conditions in some "cold cook" processes) in the presence of liquefying enzymes (e.g., alpha-amylases) to solubilize and hydrolyze the starch into dextrins. The slurry mixture is generally cooled and treated with saccharifying enzymes (e.g., glucoamylases) and yeast (e.g., *Saccharomyces cerevisiae*) to produce and convert fermentable glucose to ethanol and fermentation co-products (e.g., oil and animal feed components). Saccharification and fermentation is typically performed simultaneously. The solids in the mash are separated from the liquids and ethanol and useful co-products such as distillers' grains are obtained.

Among the recycled liquids, backset (sometimes called thin stillage) is a major component (Kwiatkowski, J. R. et al. (2006) *Industrial Crops and Products* 23:288-96). Dry grind ethanol plants typically use between anywhere from zero to 50% of liquid backset to make-up the starting substrate slurry. The backset introduces some nutritional components into the initial slurry, but also introduces components that are known stress factors for yeast, including, glycerol, lactic acid and acetic acid, which inhibit yeast growth during propagation and fermentation. Nonetheless, backset utilization is highly desirable as it reduces the requirement for fresh water.

SUMMARY

Described are compositions and methods relating to a dry grind ethanol process in which post-distillation backset is subjected to aerobic fermentation to remove components that are inhibitory to an ethanolagen, such as yeast, allowing the utilization of an increased amount of post-distillation backset during the initial preparation of starch-containing substrates for the dry grind ethanol process. Aspects and embodiments of the compositions and methods are described in the following, independently-numbered paragraphs.

1. In one aspect, a method for increasing utilization of recycled liquid backset in a dry grind ethanol process is provided, comprising: (a) hydrolyzing a starch-containing feedstock with an α-amylase in the presence of recycled liquid backset to produce a starch liquefact; (b) saccharifying the starch liquefact with a glucoamylase to produce glucose; (c) fermenting the glucose with an organism under anaerobic conditions to produce an ethanol-containing fermented mash; (d) distilling the fermented mash to recover ethanol product resulting in an ethanol-depleted, post-distillation slurry; (e) separating the solid and liquid portions of post-distillation slurry: (f) subjecting the liquid portion of the post-distillation slurry to aerobic fermentation using a non-pathogenic bacteria capable of consuming lactic acid and/or glycerol to produce post-aerobic-fermentation backset; and (g) recycling the post-aerobic-fermentation backset for use as recycled ligand backset in step (a); wherein the amount of recycled liquid backset used in step (a) is greater than the amount of backset in an otherwise identical method lacking step (f).
2. In some embodiments of the method of paragraph 1, any of steps (a)-(c) are combined or partially overlapping.
3. In some embodiments of the method of paragraph 1 or 2, any of steps (e)-(g) are combined or partially overlapping.
4. In some embodiments of the method of any of paragraphs 1-3, the non-pathogenic bacteria produce a protein of interest.
5. In some embodiments of the method of paragraph 4, the protein of interest is an α-amylase.
6. In some embodiments, the method of paragraph 4 or 5 further comprises recovering the protein of interest from the post-aerobic-fermentation backset prior to step (g).
7. In some embodiments of the method of any of paragraphs 4-6, the protein of interest is not naturally-produced by the non-pathogenic bacteria.
8. In some embodiments of the method of any of the preceding paragraphs, the non-pathogenic bacteria is a *Bacillus* sp.
9. In some embodiments of the method of any of the preceding paragraphs, the non-pathogenic bacteria is *B. subtilis* or *licheniformis*.
10. In some embodiments of the method of any of the preceding paragraphs, the non-pathogenic bacteria do not produce an endotoxin.
11. In some embodiments of the method of any of the preceding paragraphs, the non-pathogenic bacteria do not sporulate.
12. In some embodiments of the method of any of the preceding paragraphs, the organism used in (c) is a *Saccharomyces* sp.

These and other aspects and embodiments of present modified cells and methods will be apparent from the description, including any accompanying Figures.

DETAILED DESCRIPTION

I. Definitions and Abbreviations

Figure 1:
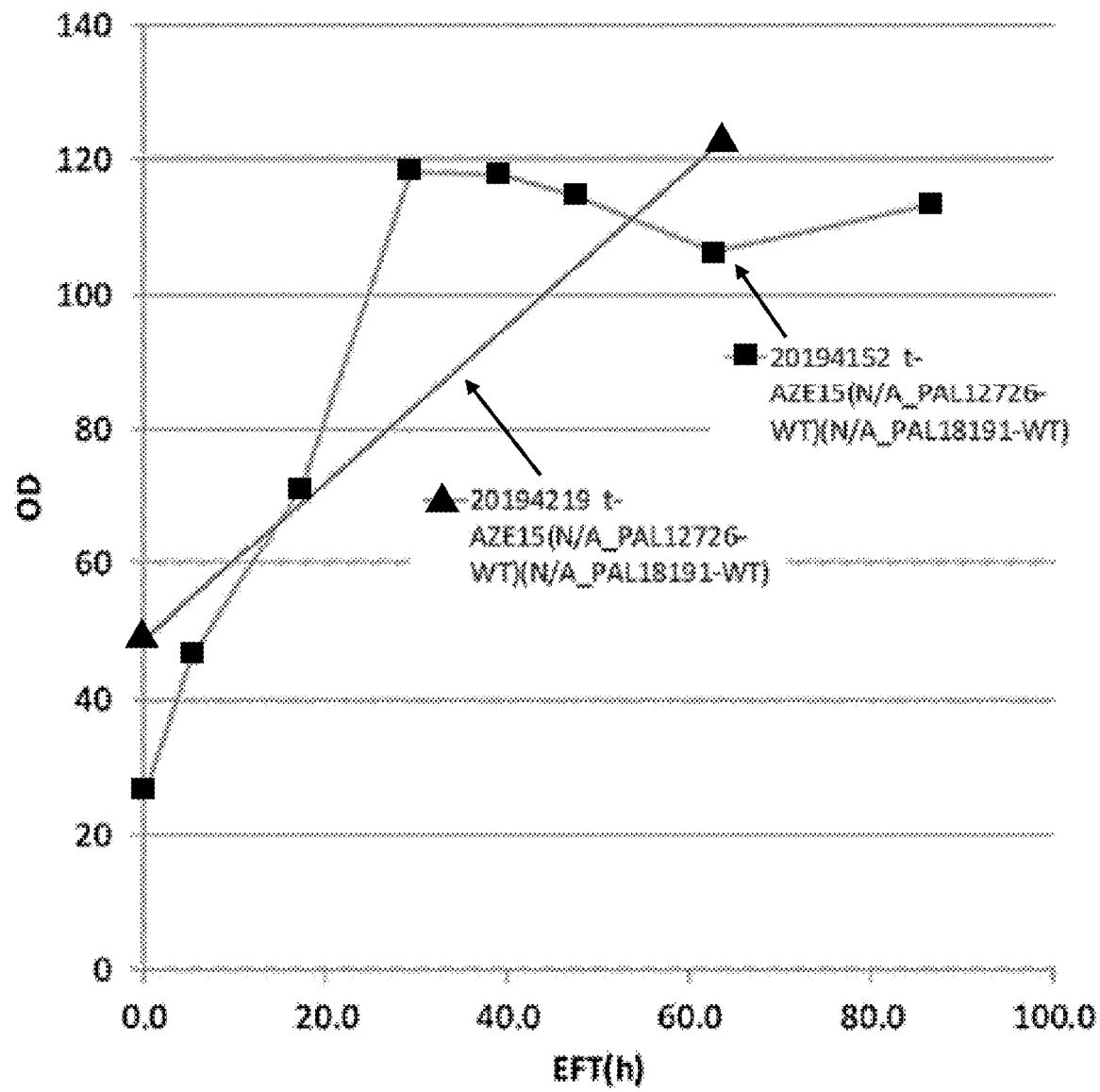
FIG. 1 is a graph showing the optical density (OD) of stillage modified by secondary aerobic fermentation compared to unmodified stillage.

Prior to describing the present strains and methods in detail, the following terms are defined for clarity. Terms not defined should be accorded their ordinary meanings as used in the relevant art.

As used herein, "liquefaction" refers to the stage in starch conversion in which gelatinized starch is hydrolyzed to give low molecular weight soluble dextrins, typically using an α-amylase.

As used herein, "saccharification" refers to enzymatic conversion of starch to glucose, typically using a glucoamylase.

As used herein, the phrase "simultaneous saccharification and fermentation (SSF)" refers to a process in the production of alcohols in which a microbial organism, such as an ethanol producing microorganism and at least one enzyme such as a granular starch hydrolyzing enzyme are in the same process step.

As used herein, "fermentation is generally the convention of sugars to valuable products, including alcohol and coproducts" using a microorganism, such as an ethanolagen.

As used herein, "backset" refers to process water, particularly stillage, which can be used to form part of the slimy for liquefaction at the front end of an ethanol production facility, typically in combination for at least some amount of fresh water. The use of backset to make up a starch slurry for liquefaction is often referred to as "recycle."

As used herein, "whole stillage" is the byproduct an ethanol production facility following distillation.

As used herein, "thin stillage" is the liquid portion of whole stillage following separation of solid materials. As used herein, "thin stillage" is also referred to as "backset" and "recycle."

As used herein, "distillers' grains (DG)" is the solid/slurry component of whole stillage.

As used herein, "distillers' dried grains (DDG) is DG that have been dried.

As used herein, "distillers' dried grains with solutes (DDGS) is DG that has been dried along with the concentrated thin stillage for added nutritional value.

As used herein, a "wet" by-product of distillation contains at least 20% water by weight.

As used herein, a "dried" by-product of distillation contains less than 20% water by weight.

As used herein, "alcohol" refers to an organic compound in which a hydroxyl functional group (—OH) is bound to a saturated carbon atom.

As used herein, "ethanolagen" refers to an organism capable of making ethanol.

As used herein, "yeast cells" yeast strains, or simply "yeast" refer to organisms from the phyla Ascomycota and Basidiomycota. Exemplary yeast is budding yeast from the order Saccharomycetales. Particular examples of yeast are *Saccharomyces* spp., including but not limited to *S. cerevisiae*. Yeast include organisms used for the production of fuel alcohol as well as organisms used for the production of potable alcohol, including specialty and proprietary yeast strains used to make distinctive-tasting beers, wines, and other fermented beverages.

As used herein, the phrase "variant yeast cells," "modified yeast cells," or similar phrases (see above), refer to yeast that include genetic modifications and characteristics described herein. Variant/modified yeast do not include naturally occurring yeast.

As used herein, the terms "polypeptide" and "protein" (and their respective plural forms) are used interchangeably to refer to polymers of any length comprising amino acid residues linked by peptide bonds. The conventional one-letter or three-letter codes for amino acid residues are used herein and all sequence are presented from an N-terminal to C-terminal direction. The polymer can be linear or branched, it can comprise modified amino acids, and it can be interrupted by non-amino acids. The terms also encompass an amino acid polymer that has been modified naturally of by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications.

As used herein, "aerobic fermentation" refers to growth in the presence of oxygen.

As used herein, "anaerobic fermentation" refers to growth in the absence of oxygen.

As used herein, the singular articles "a," "an," and "the" encompass the plural referents unless the context clearly dictates otherwise. All references cited herein are hereby incorporated by reference in their entirety. The following abbreviations/acronyms have the following meanings unless otherwise specified:

° C. degrees Centigrade
DG distillers' gains
DDG distillers' dried grains
DDGS distillers' dried grains with solutes
DNA deoxyribonucleic acid
DS dry solids
EtOH ethanol
g or gm gram
g/L grams per liter
GA glucoamylase
GAU/g DS glucoamylase units per gram dry solids
HPLC high performance liquid chromatography
hr or h hour kDa kilodalton
M molar
mg milligram
mL or ml milliliter
ml/min milliliter per minute
mN millimolar
N normal
na not applicable
PCR polymerase chain reaction
ppm parts per million
SAPU/g DS protease units per gram dry solids
SSCU/g DS fungal α-amylase units per gram dry solids
Δ relating to a deletion
μg microgram
μL and μl microliter
μM and μm micromolar II. Secondary Aerobic Fermentation to Improve Backset Quality Applicants have discovered that secondary aerobic fermentation reduces the amounts of ethanolagen-inhibitory components in post-distillation liquid backset from a dry grind ethanol facility, thereby allowing the utilization of significantly more backset during the initial preparation of starch-containing substrate slurries for the dry grind ethanol process. The benefits of using increased backset to form an initial starch slurry are several. First, fresh water savings is a significant benefit, as water usage is an increasingly important consideration for all commercial activities. Secondly, the use of recycle having reduced stress factors is likely to improve ethanolagen performance, thereby increasing ethanol and co-product production efficiency in general. thin The present inventors have demonstrated that *Bacillus* can be grown on stillage by-products. Based on OD measurements, approximately 2.8 g of dry cell weight *Bacillus* cell mass was produced per liter of stillage. This growth density can no doubt be increased with further optimization. This high level of bacterial growth can be obtained without addition of any supplements (such as salts or sugars) to the stillage, and without pH adjustment. During growth, the bacteria consumes glycerol, lactic acid and simple sugars from stillage by-products making it cleaner in terms of yeast stress components and more desirable for use as backset recycle.

III. Handling and Treatment of Backset

In practice, a portion of thin stillage (up to 100%) is sent to a secondary fermentation skid installed at a dry grind ethanol plant, from which it can be pumped into a continuous aerobic fermentation tank. In some embodiments, the thin stillage is first be sent through a heat sterilizer to reduce the amount of endogenous microorganisms present. The thin stillage is then inoculated with a bacteria suitable for growing under aerobic conditions (see, below). Thin stillage is continuously treated in this manner and, following a suitable amount of growth of the bacteria, is pumped to a drop tank. Once the continuous thin stillage aerobic culture is started, inoculation with fresh bacteria is needed only occasionally.

The additional of nutrients and salt, and pH adjustment is not needed but can be performed if desired. In some embodiments, air is pumped into the continuous thin stillage culture to assist aerobic growth. In some embodiments, ammonia is pumped into the continuous thin stillage culture as a nitrogen source.

Following bacterial growth, the treated thin stillage can be subjected to any of a number of recovery steps, such as a centrifugation, filtration and/or drying to produce a high protein syrup or dried product that may be valuable as, e.g., an animal feed additive. Where the bacteria produce a protein of interest, the protein may be recovered using conventional means.

The bulk of the aerobic thin stillage culture is used as a portion (up to 100%) of the liquid used to make up a starch slurry for a new liquefaction operation. This cycle can continue essentially indefinitely.

IV. Bacteria Suitable for Secondary Aerobic Fermentation

Bacteria suitable for use according to the present compositions and methods include non-pathogenic organisms capable of growing under aerobic conditions. In view of the large volumes of liquid backset to be potentially subjected to secondary aerobic fermentation, the absence of endotoxins and other risks associated with bacterial pathogens is critical. Only approved organisms suitable for large-scale fermentations, e.g., for protein production, should considered.

In addition, since it is likely that a portion of the modified stillage will be used in animal feed, only organisms approved by the Association of American Feed Control Officials (AAFCO) should be used. Such organisms include *Aspergillus* spp., including *A. niger* and *A. oryzae*, *Bacillus* spp., including *B. amyloliquefaciens*, *B. coagulans*, *B. lentus*, *B. licheniformis*, *B., pumilus* and *B. subtilis*, *Bacteroides* spp., including *B. amylophilus*, *B. capillosus*, *B. ruminocola* and *B. suis*, *Bifidobacterium* spp., including *B. adolescentis*, *B. animalis*, *B. bifidum*, *B. infantis*, *B. longum* and *B. thermophilum*, *Enterococcus* spp., including *E. cremoris*, *E. diacetylactis*, *E. faecium*, *E. intermedius*, *E. lactis* and *E. thermophilus*, *Lactobacillus* spp., including, *L. acidophilus*, *L. animalis*, *L. brevis*, *L. buchneri*, *L. bulgaricus*, *L. casei*, *L. cellobiosus*, *L. curvatus*, *L. delbruekii*, *L. farciminis*, *L. fermentum*, *L. helveticus*. *L. lactis*, *L. plantarum* and *L. reuteri*, *Leuconostoc* spp., including *L. mesenteroides*, *Megasphaera* spp., including *M. elsdenii*, *Pediococcus* spp., including *P. acidilactici*, *P. cerevisae* and *P. pentosaceus*, *Propionibacterium* spp., including *P. acidipropionici*, *P. freudenreichii* and *P. shermanii*, *Rhodopseudomonas* spp., including *R. palustris*. It will be appreciated that the bacteria used for aerobic fermentation are selected for their non-pathogenecity and AAFCO compliance. The bacteria are not simply contaminants, that arise during the operation of a conventional fuel ethanol facility.

The bacteria may be wild-type or genetically-engineered, in which case they may over-express an endogenous protein of interest or express an exogenous protein of interest, including a protein that provides a benefit in liquefaction. Particular proteins for use in liquefaction are thermostable α-amylases and proteases.

Suitable α-amylases are from *Bacillus* sp., including *B. stearothermophilis*, *B. licheniformis*, *B. amyloliquefactions*, and hybrids, thereof, as well as from *Cytophaga* sp. Other suitable α-amylases are from *Pyrococcus* sp. Exemplary commercially-available α-amylases are branded under the names FUELZYME™ (BASF, USA), LPHERA® and LIQUOZYME® (Novozymes, DK), and SPEZYME® (DuPont, DK).

Suitable proteases are from *Pyrococcus* and *Thermobifida*, and branded under the names OLEXA™ (Novozymes) and OPTIMASH DCO+ (DuPont).

In some embodiments, the bacterial are genetically modified or otherwise selected such that they demonstrate reduced sporulation and such that they do not sporulate.

V. Ethanolagens Suitable for Primary Anaerobic Fermentation

Ethanolagens are typically unicellular eukaryotic microorganisms, such as yeast, that are classified as members of the fungus kingdom and include organisms from the phyla Ascomycota and Basidiomycota. Yeast that can be used for alcohol production include, but are not limited to, *Saccharomyces* spp., including *S. cerevisiae*, as well as *Kluyveromyces, Lachancea* and *Schizosaccharomyces* spp. Numerous yeast strains are commercially available, many of which have been selected or genetically engineered for desired characteristics, such as high alcohol production, rapid growth rate, and the like. Numerous yeast has been genetically engineered to produce heterologous enzymes or even to include heterologous pathways. Any yeast capable of producing alcohol are believed to be candidates for modification as described.

VI. Substrates and Conditions

Alcohol production from a number of carbohydrate substrates, including but not limited to corn starch, sugar cane, cassava, and molasses, is well known, as are innumerable variations and improvements to enzymatic and chemical conditions and mechanical processes. The present compositions and methods are believed to be fully compatible with such substrates and conditions.

Numerous variations of ethanol production process exist, including cold cook, or no cook, involving liquefaction at or below the gelatinization temperature, simultaneous saccharification and fermentation, fractionation processes, and the like. None are expected to be incompatible with the present compositions and methods.

VII. Fermentation Products and Co-Products

Typical alcohol fermentation products include organic compound having a hydroxyl functional group (—OH) bound to a carbon atom. Exemplary alcohols include but are not limited to methanol, ethanol, n-propanol, isopropanol, n-butanol, isobutanol, n-pentanol, 2-pentanol, isopentanol, and higher alcohols. The most commonly made fuel alcohols are ethanol, and butanol.

Valuable by-products (or co-products) of alcohol production, and particularly dry-grind ethanol production, are products for animal feed, usually in the form of distillers' dried grains (DDG) or, more commonly, distillers' dried grains with solutes (DDGS). Such animal feed products are in many ways more nutritional than the initial feed-stocks used for ethanol production as they are depleted for carbohydrates but enriched for amino acids derived both from the feedstock and the fermenting organism (i.e., ethanolagen).

The present compositions and methods are likely to alter the nutritional value of fermentation co-products to animals, including fermentation broth, whole stillage, thin stillage, distillers dried grains, distillers dried grains with solutes, condensed distillers solubles or other protein-containing post fermentation coproducts.

These and other aspects and embodiments of the present strains and methods will be apparent to the skilled person in view of the present description. The following examples are intended to further illustrate, but not limit, the strains and methods.

EXAMPLES

Example 1: Aerobic Growth of a Non-Pathogenic Bacteria in Stillage

The use of modified post-distillation liquid (backset; recycle) on fermentation performance was studied using conventional, unmodified backset as a control. Actual post-distillation backset from a commercial dry grind ethanol plant was collected and frozen to be used in a laboratory-scale experiment. The frozen backset was thawed and incubated at 65° C. for 3 hours to essentially pasteurize the backset to kill existing organisms.

Experiments were performed in batch, accellerostat or chemostat mode, with appropriate controls for each. For batch experiments, 200 g of thawed substrate was put into a 250 mL DASBOX® fermentation vessel (Eppendorf, New York, USA). For accellerostat and chemostat mode, approximately 2 L of thawed 600 micron sieved backset ("feed") was put into a bottle with a magnetic stir bar and tubing was connected to allow for pumping with a peristaltic pump into separate 250 mL DASBOX® fermentation vessels.

For accellerostat and chemostat operation conditions, the fermentation vessels were set up with two minor modifications. The first was to include a T-connector to allow the backset to be fed into the fermentation vessels using the air inlet. This was done to prevent any back growth of organisms in the usual feed line, unnecessarily contaminating standard equipment. The second was to replace the condenser, normally located on the top of the fermenter, with an overflow tube. The tube sat at a level that allowed for approximately 73 mL of liquid to be in the vessel when at full agitation and full air flow. Air entering the vessel would entrain any excess fluid and send it out of the fermenter to be handled as waste. The overflow tube was connected to a 1 L collection bottle on dry ice, which allowed the liquid and off-gas to be separated. The dry ice simply froze the liquid to preserve further growth of organisms. The off-gas went through a condenser to remove water and then to a mass spectrometer for analysis.

During the experiment under accellerostat and chemostat operation conditions, backset would be fed to the fermenter at a constant rate or be continuously varied depending on the purpose of the experiment. In an experiment to collect a sample for laboratory feed analysis, the feed rate was adjusted to achieve a dilution rate of approximately 0.25/h. In an experiment to evaluate how the strain performs, the feed rate was adjusted to achieve a dilution rate of 0-10/h up to 0.55/h with a rate of change of 0.01/h/h.

Target pH of the fermentation vessels was maintained using 28% ammonium hydroxide or 10% sulfuric acid. Target temperature was maintained using thermoelectric heater and cooler. Targeted dissolved oxygen was controlled using agitation and supplemental oxygen.

Stillage was inoculated in batch, accellerostat and chemostat modes using a publically-available *Bacillus subtilis* strain (strain designation CB354, alias t-AZE16), available through American Type Culture Collection as ATCC6051 modified to prevent sporulation by the deletion of the spoIIE and srfA genes. Temperature and pH were maintained at 37° C. and 7.4, respectively.

FIG. 1 shows the optical density (OD) of the stillage cultures measured at 550 nm. Runs 20194152 and 20194219 showed a significant increase in OD, indicating cell growth. Run 20194130 was performed in batch mode and OD was not measured. The pH profiles of the different stillage samples were generally maintained in the range of 7.2-7.8 with Run 20194152, and to a lesser degree, Run 20194219, showing increased tendency to become more alkaline (data not shown).

Figure 2:
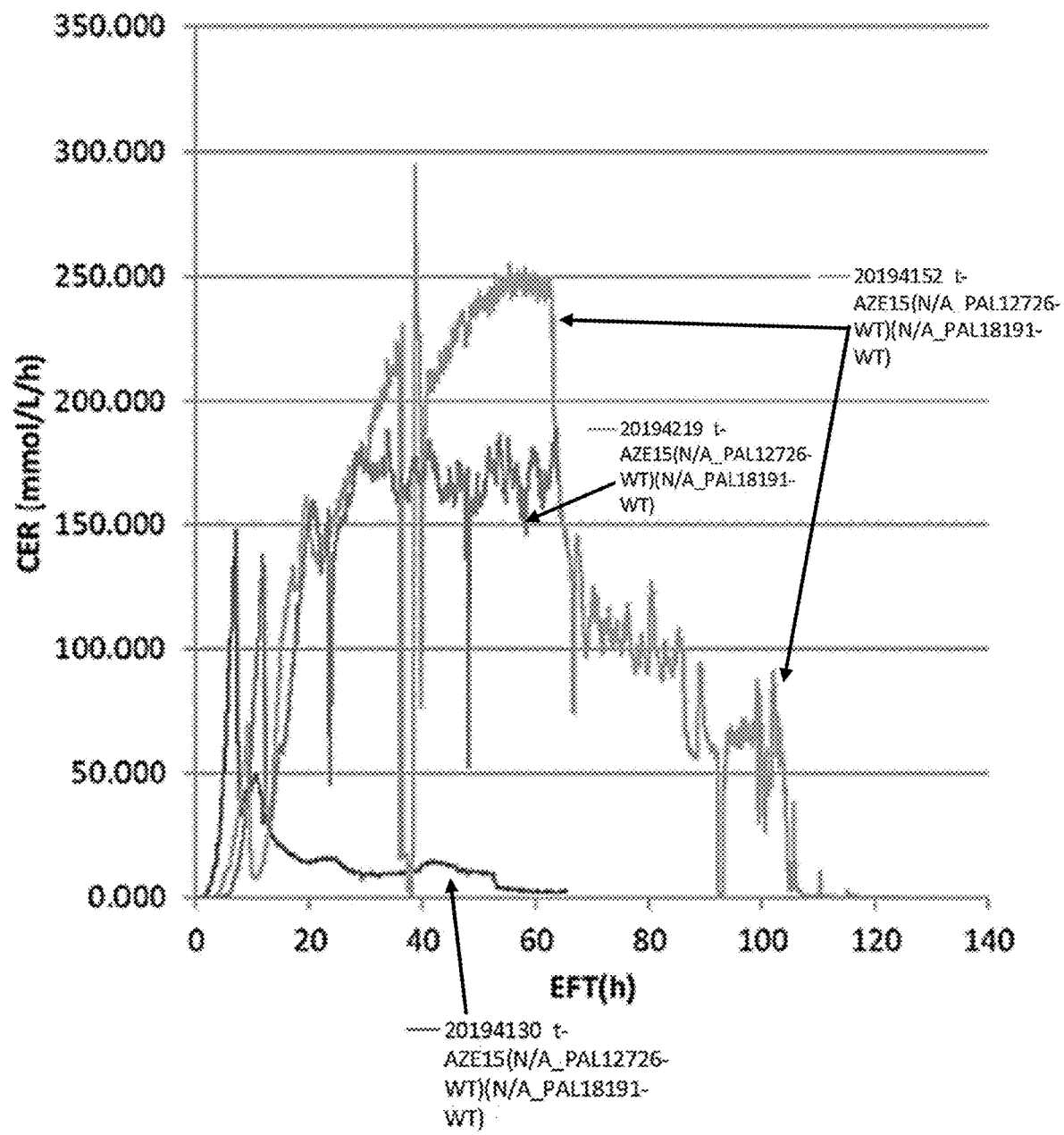
FIG. 2 is a graph showing the carbon dioxide evolution rate (CER) profile of stillage modified by secondary aerobic fermentation compared to unmodified stillage.

FIG. 2 shows the carbon dioxide evolution rate (CER) profile for the three different runs. Runs 20194152 and 20194219 showed a significantly increased CER again indicating that the organism was growing on the stillage substrate. Run 20194130 did not show an increase in CER as this run was a batch experiment performed to confirm the strain would respire on backset.

Example 2: Effect of Modified Recycle on Liquefaction and Fermentation

Modified and unmodified backset were used to prepare starch-containing substrates for liquefaction and subsequent fermentation in a new dry grind ethanol production batch process. One substrate for liquefaction was prepared by weighing 340 g of the ground corn and adding 660 g modified backset and the other was prepared by weighing 340 g of the ground corn and adding 660 g unmodified backset, both at pH 5-2. Each substrate was subjected to liquefaction at 85° C. for 2 hr using α-amylase (SPEZYME® HT, DuPont) at 0.4 kg/MT dosage.

The resulting liquefacts were cooled to room temperature and the pH adjusted to pH 4.8 with sulfuric acid. Saccharifying enzymes i.e., glucoamylase were added at a dosage equivalent to 0.325 GAUs/g ds with constant mixing along with protease (i.e., FERMGEN™; DuPont) at 0.0030% w/w. The liquefacts were apportioned into 125 mL Erlenmeyer flasks in 100 g quantities with 600 ppm urea added as a nitrogen source for the ethanolagen. Commercially-available active dry yeast (ETHANOL RED®; Lesaffre, Milwaukee, WI, USA) was added at 0.01% w/w dosage to all flasks and incubated under anaerobic conditions.

The initial weights of the flasks were recorded and the flasks were placed in air heated incubators at 32° C. at 200 rpm for 62 hr. Weights were routinely recorded at 16, 24, 40, 48 and 62 hr of incubation to measure weight loss due to the production of ethanol and evolution of $CO_2$. Samples taken at the end of fermentation at 62 hr were processed and prepared using standard methods for HPLC analysis to measure the concentrations of ethanol, glycerol, sugar and organic acid.

The results of HPLC analysis are shown in Tables 1 and 2. The results show that modified backset was more suitable for fermentation when added as even as much as 100% of the recycle liquid used for preparing an initial when preparing the substrate. The treatment with modified backset resulted in faster fermentation rates and higher ethanol concentration with significantly lower glycerol and lactic acid levels, which improves the carbon conversion fermentation efficiency of the yeast.

TABLE 1

Weight loss measurement (g) during SSF with substrate prepared using modified and unmodified backset

| Treatment | Hours | | | | |
|---|---|---|---|---|---|
| | 16 | 24 | 40 | 48 | 67 |
| None | 5.87 | 8.22 | 10.30 | 10.61 | 10.94 |
| Modified | 7.20 | 8.69 | 10.56 | 10.84 | 11.14 |

TABLE 2

Concentrations (% w/v) of metabolites in modified and unmodified backset

| Treatment | Hours | Lactic acid % w/v | Glycerol % w/v | Ethanol % w/v |
|---|---|---|---|---|
| None | 62 | 0.17 | 2.51 | 12.88 |
| Modified | 62 | 0.06 | 1.00 | 13.02 |

Example 3: Production of Enzymes During the Modification of the Post-Distillation Liquid The use of modified post-distillation liquid modified by aerobic fermentation with a bacteria capable of expressing a recombinant protein activity on liquefaction performance was studied using conventional, unmodified backset as a control. As before, post-distillation backset from a commercial dry grind ethanol plant was collected and frozen to be used in a laboratory-scale experiment.

Figure 3:
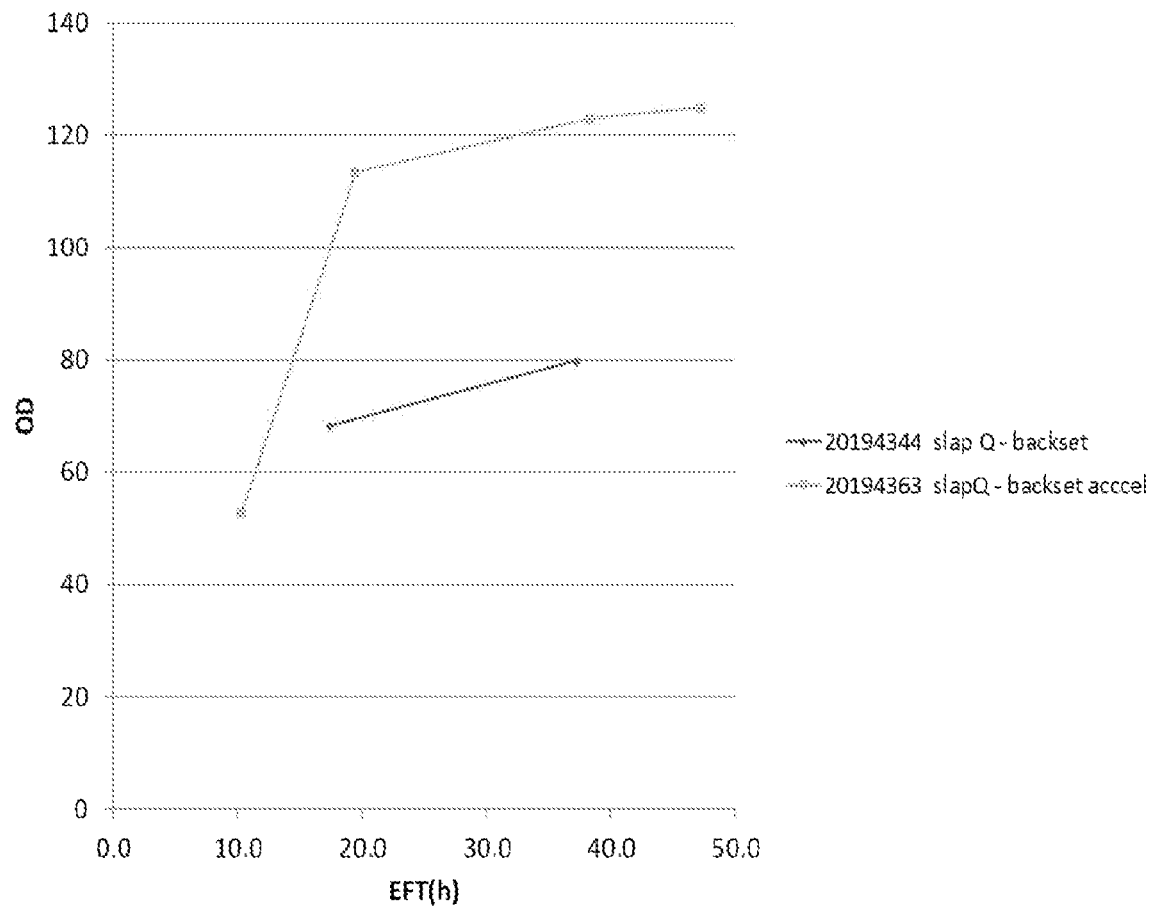
FIG. 3 is a graph showing the OD of stillage modified by secondary aerobic fermentation compared to unmodified stillage.

The backset was subjected to aerobic fermentation with a *Bacillus licheniformis* strain producing a commercially-available α-amylase (SPEZYME® ALPHA (SLAP-Q); DuPont) using a DASBOX® fermentation vessel, as before. Stillage was inoculated with the *Bacillus* strain in both batch (Run 20194344) and accellerostat (Run 20194363) mode. Temperature and pH were maintained at 42° C. and 7.0, respectively. FIG. 3 shows the increase in stillage OD as a result of inoculation with the *Bacillus*, indicating bacterial growth.

Figure 4:
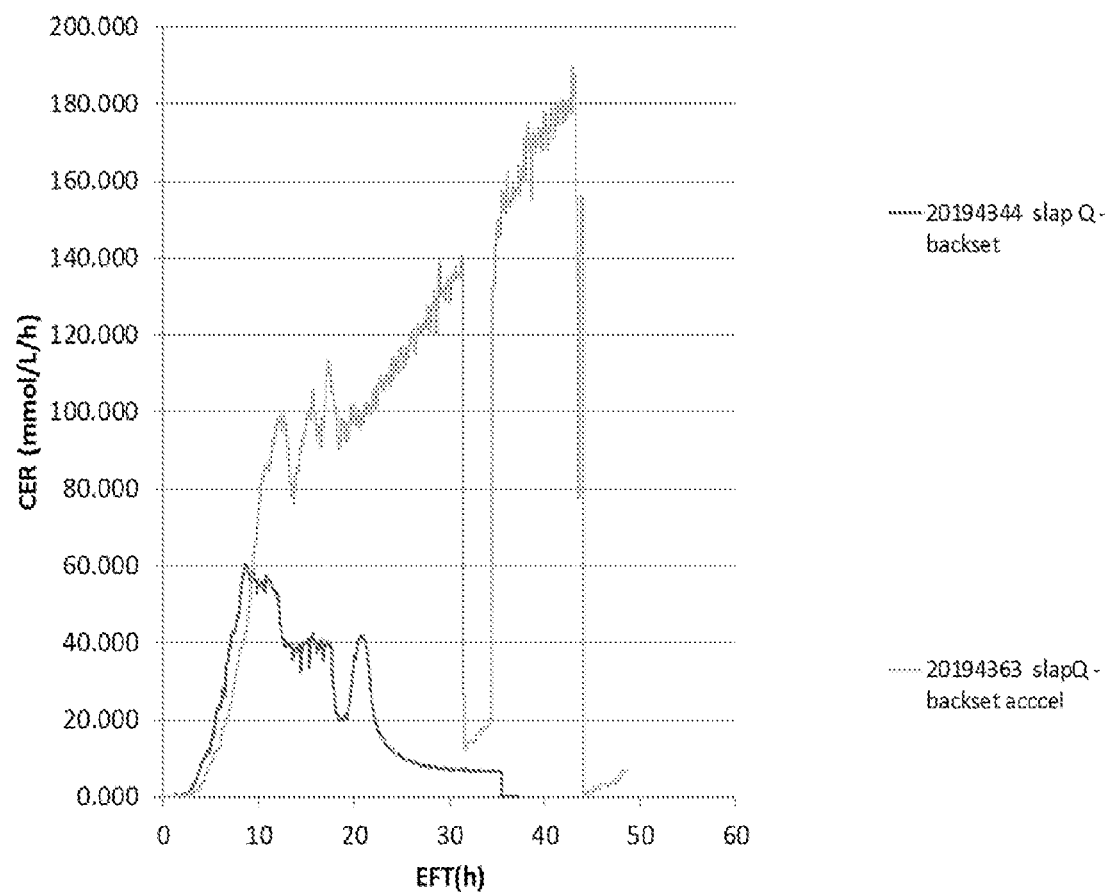
FIG. 4 is a graph showing the CER profile of stillage modified by secondary aerobic fermentation compared to unmodified stillage.
Figure 5:
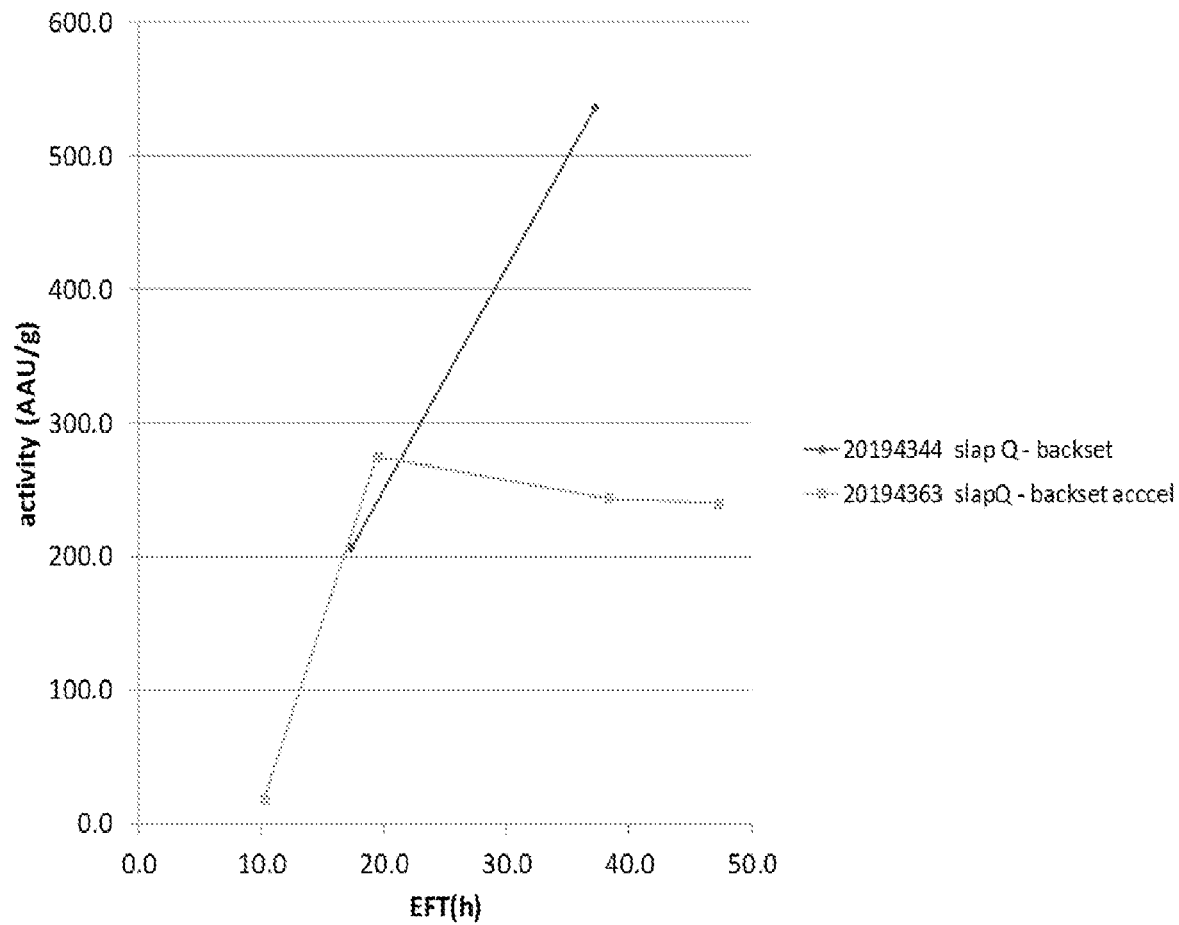
FIG. 5 is a graph showing α-amylase activity in stillage modified by secondary aerobic fermentation using a recombinant *Bacillus* compared to unmodified stillage.

FIG. 4 shows the carbon dioxide evolution rate (CER) profile for the different runs. Run 20194363 showed a significant increase CER, again indicating that the organism was growing on the stillage substrate. Run 20194344 showed a much less significant increase in CER as it was a batch experiment to determine if the organism could grow or produce any enzyme. At approximately 30 h and 42 h, the accellerostat experiment experienced a blockage. The blockage at 42 h essentially ended the experiment.

The α-amylase activity of samples was monitored during the run. Due to the continuous nature of production in run 20194363, it had a higher productivity, 70.2 mg α-amylase/L broth/h, even though the enzyme concentration was lower than run 20194344 at 9.1 mg α-amylase/L/h.

Example 4: Liquifaction Using Modified Backset Containing a Recombinant Enzyme Modified and unmodified backset were used to prepare ground corn substrate to test the performance in viscosity reduction in liquefaction using a Rapid Visco Analyzer (RVA).

Figure 6:
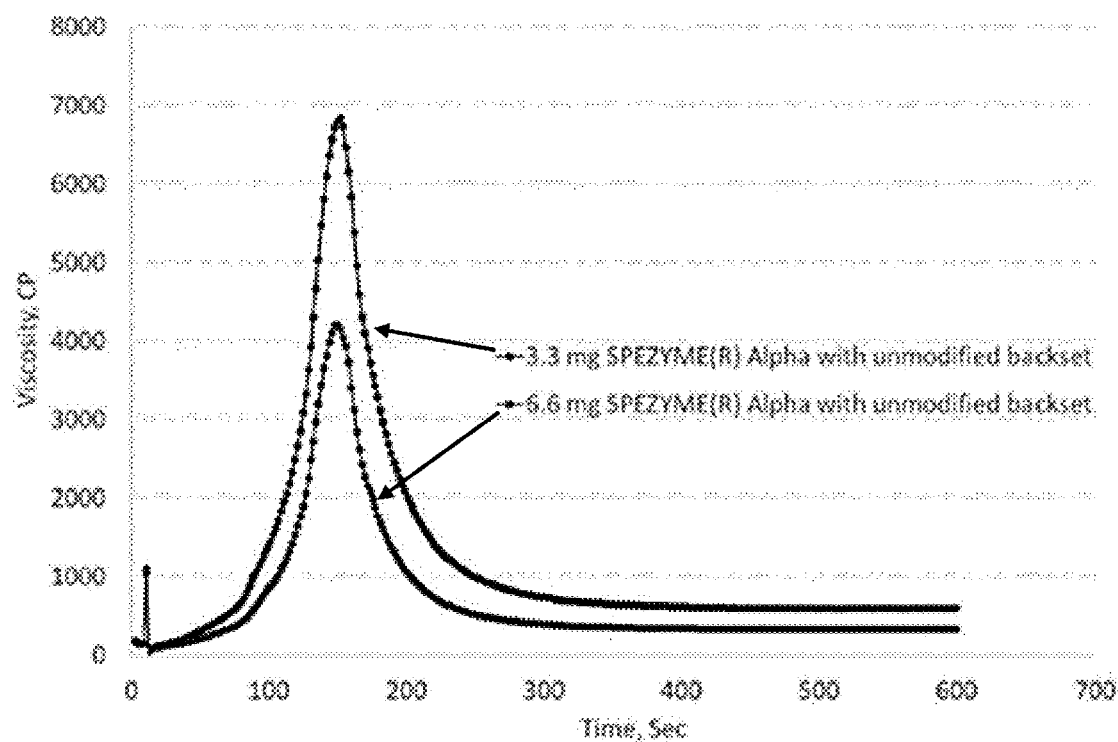
FIG. 6 is a graph showing peak and final viscosities during corn flour slimy gelatinization using two different amounts of α-amylase: 3.3 mg (circles) and 6.6 mg (squares).

9.27 grams of ground corn flour with 11% moisture content was mixed with 23.73 grams of unmodified backset (25% DS) in two RVA sample cups, and pH was adjusted to 5.5 with 1 N $H_2SO_4$. 3.3 and 6.6 milligrams of α-amylase (SPEZYME® ALPHA) were added in first and second RVA cups, respectively. 3.3 mg α-amylase is equivalent to ~5.6 AAUs/g ds and 6.6 mg α-amylase is equivalent to ~11.2 AAUs/g ds. Changes in viscosity were monitored using RVA at constant temperature set at 95° C. Unsurprisingly, liquefaction performed using the higher α-amylase dosage resulted in lower peak and final viscosities during corn flour slurry gelatinization and pasting steps (FIG. 6).

A similar experiment was performed using the modified backset in which α-amylase was produced. In three RVA sample cups, 9.27 grams of ground corn flour was mixed with 23.5, 23.6 and 23.7 grams of DI water in three RVA sample cups, respectively and the pH was adjusted to 5.5 with 1 N $H_2SO_4$. Following this modified backset was added in the three RVA cups in an amount of 0.2, 0.1 and 0.05 g (i.e., 12.99, 6.50 and 3.25 AAUs/g ds respectively).

Figure 7:
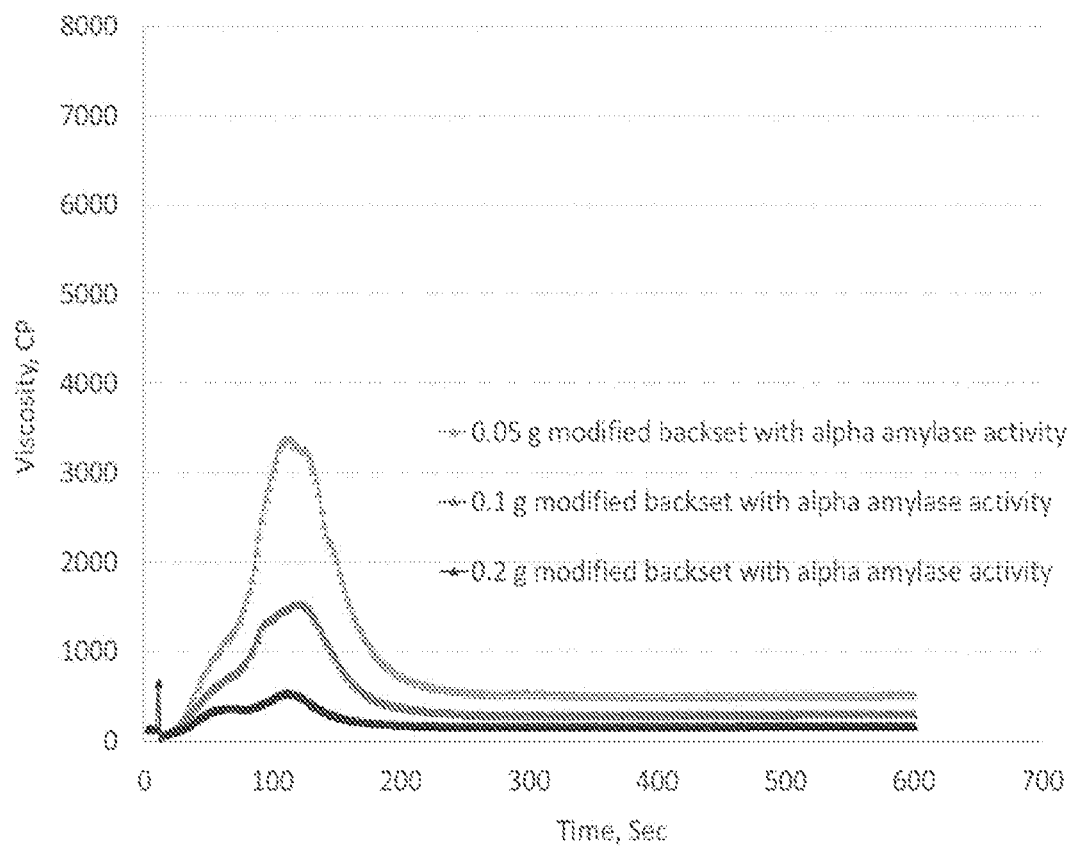
FIG. 7 is a graph showing peak and final viscosities during corn flour slurry gelatinization using different amounts of modified backset with α-amylase activity: 0.05 g (circles, light grey), 0.1 g (squares, medium grey) and 0.2 g (triangles, black).

As shown in FIG. 7, addition of modified backset was successful in reducing the peak viscosity during the corn flour slurry gelatinization and pasting steps without the addition of addition exogenous α-amylase polypeptide product. This demonstrates that the modified backset resulting from aerobic fermentation of bacterial strain capable of producing α-amylase activity could be used in corn liquefaction, allowing the use of a reduced amount of, or eliminating the need for, additional α-amylase to the liquefaction.

What is claimed is:

1. A method for increasing utilization of recycled liquid backset in a dry grind ethanol process, comprising:
    (a) hydrolyzing a starch-containing feedstock with an α-amylase in the presence of recycled liquid backset to produce a starch liquefact;
    (b) saccharifying the starch liquefact with a glucoamylase to produce glucose;
    (c) fermenting the glucose with an organism under anaerobic conditions to produce an ethanol-containing fermented mash;
    (d) distilling the fermented mash to recover an ethanol product resulting in an ethanol-depleted, post-distillation slurry;
    (e) separating the solid and liquid portions of the post-distillation slurry;
    (f) subjecting the liquid portion of the post-distillation slurry to aerobic fermentation using a non-pathogenic bacteria capable of consuming lactic acid and/or glycerol to produce a post-aerobic-fermentation backset; and
    (g) recycling the post-aerobic-fermentation backset for use as recycled liquid backset in step (a);
    wherein the amount of recycled liquid backset used in step (a) is greater than the amount of backset in an otherwise identical method lacking step (f).

2. The method of claim 1, wherein step (b) and step (c) are combined to perform simultaneous saccharification and fermentation.

3. The method of claim 1, wherein the non-pathogenic bacteria produce a protein of interest.

4. The method of claim 3, wherein the protein of interest is an α-amylase.

5. The method of claim 3, further comprising recovering the protein of interest from the post-aerobic-fermentation backset prior to step (g).

6. The method of claim 3, wherein the protein of interest is not naturally-produced by the non-pathogenic bacteria.

7. The method of claim 1, wherein the non-pathogenic bacteria is a *Bacillus* sp.

8. The method of claim 1, wherein the non-pathogenic bacteria is *B. subtilis* or *licheniformis*.

9. The method of claim 1, wherein the non-pathogenic bacteria do not produce an endotoxin.

10. The method of claim 1, wherein the non-pathogenic bacteria do not sporulate.

11. The method of claim 1, wherein the organism used in step (c) is a *Saccharomyces* sp.

* * * * *